US009421553B2

(12) United States Patent
Dionne et al.

(10) Patent No.: US 9,421,553 B2
(45) Date of Patent: *Aug. 23, 2016

(54) HIGH-VOLUME FAST SEPARATION OF MULTI-PHASE COMPONENTS IN FLUID SUSPENSIONS (75) Inventors: Jason Dionne, Simsbury, CT (US); Bart Lipkens, Hampden, MA (US); Edward A. Rietman, Nashua, NH (US)

(73) Assignee: FloDesign Sonics, Inc., Wilbraham, MA (US)

( * ) Notice: Subject to any disclaimer, the term of this patent is extended or adjusted under 35 U.S.C. 154(b) by 562 days.

This patent is subject to a terminal disclaimer.

(21) Appl. No.: 13/216,049

(22) Filed: Aug. 23, 2011

(65) Prior Publication Data
US 2012/0325727 A1  Dec. 27, 2012

Related U.S. Application Data (60) Provisional application No. 61/402,079, filed on Aug. 23, 2010.

(51) Int. Cl.
*B03B 5/00* (2006.01)
*C02F 1/36* (2006.01)
(Continued)

(52) U.S. Cl.
CPC ............... *B03B 5/00* (2013.01); *B01D 21/283* (2013.01); *C02F 1/36* (2013.01); *C12M 47/02* (2013.01)

(58) Field of Classification Search
CPC ........ B01D 21/28; B01D 21/283; B03B 5/00; C02F 1/34; C02F 1/36
USPC .................... 209/155, 156; 422/20, 292, 306; 210/748.01–748.05, 321.6–321.9
See application file for complete search history.

(56) References Cited

U.S. PATENT DOCUMENTS 4,165,273 A   8/1979   Azarov et al.
5,085,783 A   2/1992   Feke et al.
(Continued)

FOREIGN PATENT DOCUMENTS

WO   WO 00/41794 A1   7/2000
WO   WO-2009111276 A1   9/2009

OTHER PUBLICATIONS

B. Lipkens, J. Dionne, A. Trask, B. Szczur, A. Stevens, E. Rietman, "Separation of micron-sized particles in macro-scale cavities by ultrasonic standing waves," Presented at the International Congress on Ultrasonics, Santiago, Jan. 11-17, 2009.
(Continued)

*Primary Examiner* — Joseph C Rodriguez
*Assistant Examiner* — Kalyanavenkateshware Kumar
(74) *Attorney, Agent, or Firm* — Richard M. Klein; Fay Sharpe LLP (57) ABSTRACT A flow chamber is provided through which is flowed a mixture of a fluid and a particulate. The flow chamber comprises at least one multi-phase water inlet through which multi-phase water enters the flow chamber, a water outlet through which water exits the flow chamber, a solids outlet through which particles having a density at or above a pre-defined threshold exit the flow chamber, and a low density outlet through which particles having a density below the pre-defined threshold exit the flow chamber. Also provided are one or more ultrasonic transducers and one or more reflectors corresponding to each transducer to acoustically filter the fluid and cause particles/fluid to be selectively diverted to one of the outlets. Related apparatus, systems, techniques and articles are also described.

26 Claims, 11 Drawing Sheets (51) Int. Cl.
  *B01D 21/28* (2006.01)
  *C12M 1/00* (2006.01)

(56) References Cited

U.S. PATENT DOCUMENTS

| | | | |
|---|---|---|---|
| 5,225,089 A | | 7/1993 | Benes et al. |
| 5,711,888 A | * | 1/1998 | Trampler et al. ........ 210/748.05 |
| 6,482,327 B1 | * | 11/2002 | Mori et al. .................... 210/695 |
| 6,487,095 B1 | | 11/2002 | Malik et al. |
| 2002/0134734 A1 | | 9/2002 | Campbell et al. |
| 2003/0230535 A1 | | 12/2003 | Affeld et al. |
| 2006/0037915 A1 | * | 2/2006 | Strand et al. .................. 210/748 |
| 2007/0272618 A1 | | 11/2007 | Gou et al. |
| 2008/0217259 A1 | | 9/2008 | Siversson |
| 2009/0178716 A1 | * | 7/2009 | Kaduchak et al. .............. 137/13 |
| 2009/0226994 A1 | | 9/2009 | Lemor et al. |
| 2010/0000945 A1 | | 1/2010 | Gavalas |
| 2010/0206818 A1 | | 8/2010 | Leong et al. |
| 2011/0123392 A1 | | 5/2011 | Dionne et al. |
| 2011/0154890 A1 | | 6/2011 | Holm et al. |

OTHER PUBLICATIONS

B. Lipkens, J. Dionne, A. Trask, B. Szczur, and E. Rietman, "Prediction and measurement of particle velocities in ultrasonic standing waves," J. Acoust. Soc. Am. 124, No. 4, pp. 2492 (A) 2008.

B. Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008.

B. Lipkens, M. Costolo, and E. Rietman, "The effect of frequency sweeping and fluid flow on particle trajectories in ultrasonic standing waves", IEEE Sensors Journal, vol. 8, No. 6, pp. 667-677, 2008.

Castro, V. E., "Tunable gap and quantum quench dynamics in bilayer graphene"; Jul. 13, 2010, Mathematica Summer School.

Garcia-Lopez, "Enhanced Acoustic Separation of Oil-Water Emulsion in Resonant Cavities", The Open Acoustics Journal, pp. 66-71, 2008.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

L. P. Gor'kov, "On the forces acting on a small particle in an acoustical field in an ideal fluid," Soy. Phys. Dokl., vol. 6, pp. 773-775, 1962.

Meribout, et al., "An Industrial-Prototype Acoustic Array for Real-Time Emulsion Layer Detection in Oil Storage Tanks", IEEE Sensors Journal, vol. 9, No. 12, Dec. 2009.

Pangu, et al., "Droplet transport and coalescne kinetecs in emulsions subjected to acoustic fields", Ultrasonics 46, pp. 289-302 (2007).

Ponomarenko et al. "Density of states and zero Landau level probed through capacitance of graphene"; Nature Nanotechnology Letters; Jul. 5, 2009; DOI: 10.1038/NNANO.2009.177.

Sony News Release: <http://www.sony.net/SonyInfo/News/Press/201010/10-137E/index.html>.

International Search Report dated Nov. 16, 2012.

Extended European Search Report for European Application No. 12825592.4 dated Apr. 28, 2015.

* cited by examiner

FIG. 4D Oil separation

FIG. 4C Bacterial Spores (1 μm)

FIG. 4B Microalgae (10 μm)

FIG. 4A Iron-Oxide (20 μm)

FIG. 11

HIGH-VOLUME FAST SEPARATION OF MULTI-PHASE COMPONENTS IN FLUID SUSPENSIONS

RELATED APPLICATION

This application claims priority to U.S. Pat. App. Ser. No. 61/402,079 filed on Aug. 23, 2010, the contents of which are hereby fully incorporated by reference.

TECHNICAL FIELD

The subject matter described herein relates to techniques for separating multiphase components within fluid suspensions such as water.

BACKGROUND

Numerous processes require the removal of solids, microorganisms, and oils that are suspended in a water matrix. For example, water can include suspended oils and dirt which must be removed for human use either for irrigation, or industrial processes, or recycling. However, accurate removal or separation of particles from water can be costly and/or time consuming especially when high volumes of water are being treated.

SUMMARY

In one aspect, a flow chamber is provided through which is flowed a mixture of a fluid and a particulate. The flow chamber comprises at least one multi-phase water inlet through which multi-phase water enters the flow chamber, a water outlet through which water exits the flow chamber, a solids outlet through which particles having a density at or above a pre-defined threshold exit the flow chamber, and a low density outlet through which particles having a density below the pre-defined threshold exit the flow chamber. Also provided are one or more ultrasonic transducers and one or more reflectors corresponding to each transducer. Each transducer forms a standing acoustic wave at a different ultrasonic frequency and each ultrasonic frequency is optimized for a specific range of particle sizes to, along with a geometry of the flow chamber, selectively separate particles from the multi-phase water and water so that such particles exit the flow chamber via one of the solids outlet and the low density outlet.

The one or more ultrasonic transducers operate at a frequency in a range of 1 MHz to 10 MHz, and in some implementations, the one or more ultrasonic transducers operate at a frequency in a range of 100 kHz to 20 MHz. The one or more ultrasonic transducers can be embedded in a wall of the flow chamber. The one or more ultrasonic transducers can be arranged in a flat series. In arrangements with multiple transducers, the transducers can be arranged in a parallel array within an inner portion of the flow chamber.

The flow chamber can be vertically oriented (relatively to gravity) with the low density outlet being on an upper portion and the solids outlet being on a lower portion. In other implementations, the flow chamber can be horizontally oriented with the low density outlet being on the upper portion and the solids outlet being on the lower portion. The flow chamber can alternatively be diagonally oriented with the low density outlet being on the upper incline and the solids outlet being on the lower incline. With a diagonal arrangement, the multi-phase water inlet can be at an obtuse angle from an outer wall of the flow chamber relative to the solids outlet.

The multi-phase water inlet can be disposed between the low density outlet and the two or more ultrasonic transducers. The multi-phase water inlet can be at an acute angle from an outer wall of the flow chamber relative to the solids outlet. The water outlet can be disposed between the two or more ultrasonic transducers and the solids outlet.

The particles can be selected from a group comprising: microalgae, yeast, fungi, bacteria, spores, gases or oils, metal oxides, metal particles, clays, dirt, plastics, and any particulate with a non-zero contrast factor. In arrangement with multiple transducers, each transducer can be optimized for a specific range of particles (which can be mutually exclusive) selected from a group consisting of microalgae, yeast, fungi, bacteria, spores, gases or oils, metal oxides, metal particles, clays, dirt, plastics, and any particulate with a non-zero contrast factor.

The one or more ultrasonic transducers can each generate acoustic standing waves perpendicular, to the direction of the mean flow in the flow channel. In other arrangements, the one or more acoustic standing waves have a or a vertical horizontal orientation. The one or more acoustic standing waves can exert acoustic radiation force on the particulate for which the ultrasonic frequency is optimized for, such that the particulate is trapped in its corresponding acoustic standing wave against a fluid drag force such that the particulate is concentrated in the acoustic field over time.

In addition, the solids outlet can be tapered. The flow chamber can be oriented such that the multi-phase water is gravity fed from the multi-phase water inlet towards the solids outlet.

In another aspect, a method of separating particulate from a fluid is provided that comprises: flowing the fluid past one or more positions within a flow chamber and forming acoustic standing waves at the one or more positions. In such an arrangement, each standing acoustic wave is maintained at a different ultrasonic frequency such that each ultrasonic frequency is optimized for a specific range of particle sizes and wherein particulate of the optimized size is trapped in its corresponding acoustic standing wave against the flow of the fluid, thereby concentrating the particulate in its corresponding acoustic standing wave. With such an arrangement, the flow chamber can comprise at least one multi-phase water inlet through which multi-phase water enters the flow chamber, a water outlet through which water exits the flow chamber, a solids outlet through which particles having a density at or above a pre-defined threshold exit the flow chamber, and a low density outlet through which particles having a density below the pre-defined threshold exit the flow chamber.

In yet another aspect, an apparatus includes a flow chamber through which is flowed a mixture of a fluid and a particulate. The flow chamber comprises at least one multi-phase water inlet through which multi-phase water enters the flow chamber, a water outlet through which water exits the flow chamber, a solids outlet through which agglomerated microorganisms and dirt exit the flow chamber, and a low density outlet through which agglomerated oil droplets exit the flow chamber. Also included can be one or more ultrasonic transducers, and one or more reflectors corresponding to each transducer. With this arrangement, each transducer forms a standing acoustic wave at a different ultrasonic frequency and each ultrasonic frequency is optimized for a specific range of particle sizes to, along with a geometry of the flow chamber, selectively separate particles from the multi-phase water and water so that such particles exit the flow chamber via one of the solids outlet and the low density outlet.

The current subject matter provides many advantages. For example, it allows for the efficient trapping, concentrating, and separation of various types of suspended particles, microorganisms and droplets from a host medium such as water.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
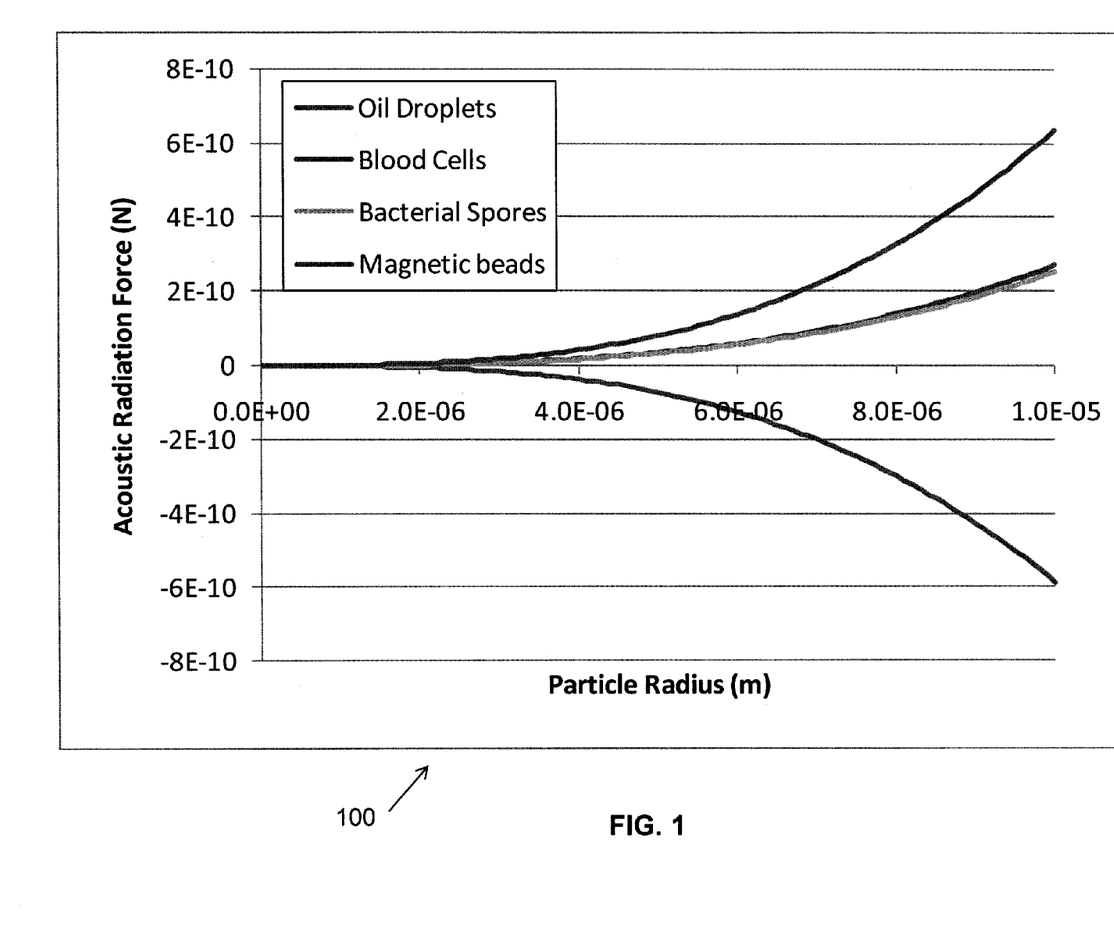
FIG. 1 is a diagram illustrating acoustic contrast, particle radius, and acoustic radiation force on particles for a given frequency of excitation and acoustic pressure level.

The current subject matter utilizes acoustophoresis, a low-power, no-pressure-drop, no-clog, solid-state approach to particle removal from fluid dispersions: i.e., it is used to achieve separations that are more typically performed with porous filters and centrifuges, but it has none of the disadvantages of these systems. For example, the diagram 100 of FIG. 1 shows the acoustic radiation forces acting on a suspended particle for an applied acoustic frequency of 1 MHz (typical for an ultrasonic transducer) and an acoustic pressure of 0.5 MPa maximum at the antinodes (readily achieved in water). Achievement of higher applied acoustic frequencies and higher acoustic pressures is possible with modern electronic drives, transducers, and intermediate matching layers. Examples of acoustic filters utilizing acoustophoresis can be found in commonly owned U.S. patent application Ser. Nos. 12/947,757, 61/261,686, 13/085,299 and 61/342,307, the contents of all of these applications are hereby fully incorporated by reference.

The acoustic radiation force ($F_{ac}$) acts on the secondary-phase particles (or fluid droplets), pushing them to the nodes (or antinodes) of the acoustic standing wave. The magnitude of the force depends on the particle density and compressibility relative to the fluid medium, and increases with the particle volume. The diagram 100 of FIG. 1 illustrates the acoustic force that operates on four different secondary phases in water as a function of the particle (or droplet) radius. The four secondary phases are hexanes (a mixture of hydrocarbons, a model for oils), red blood cells (a model for biological cells), bacterial spores (a model for "large" protein clusters and polystyrene beads such as are used for flow cytometry), and paramagnetic polystyrene beads (used for various biological capture and separation protocols). Parameters used in the calculation of the acoustic force are given below in Table 1.

The current subject matter is advantageous in that it uses acoustophoresis for separations in extremely high volumes and in flowing systems with very high flow rates. Separations have been done for micron-size particles, for which the acoustophoretic force is quite small. For example, B. Lipkens, J. Dionne, A. Trask, B. Szczur, A. Stevens, E. Rietman, "Separation of micron-sized particles in macro-scale cavities by ultrasonic standing waves," Presented at the International Congress on Ultrasonics, Santiago, Jan. 11-17, 2009; and B. Lipkens, J. Dionne, M. Costolo, A. Stevens, and E. Rietman, "Separation of bacterial spores from flowing water in macro-scale cavities by ultrasonic standing waves", (Arxiv) June 2010, the contents of both papers are hereby fully incorporated by reference) show that *Bacillus cereus* bacterial spores (a model for anthrax) have been trapped at 15% efficiency in an acoustophoretic cavity embedded in a flow system that can process drinking water at rates up to 120 mL/minute (1 cm/second linear flow). The concentration ratio has been as high as 1000 in a single-pass, small-scale prototype acousto-collector. The techniques described in this paper will scale up to higher flow rates or larger flow channel, which has been proven in a 6"×6" system and processing to 12" in dimension.

Figure 2:
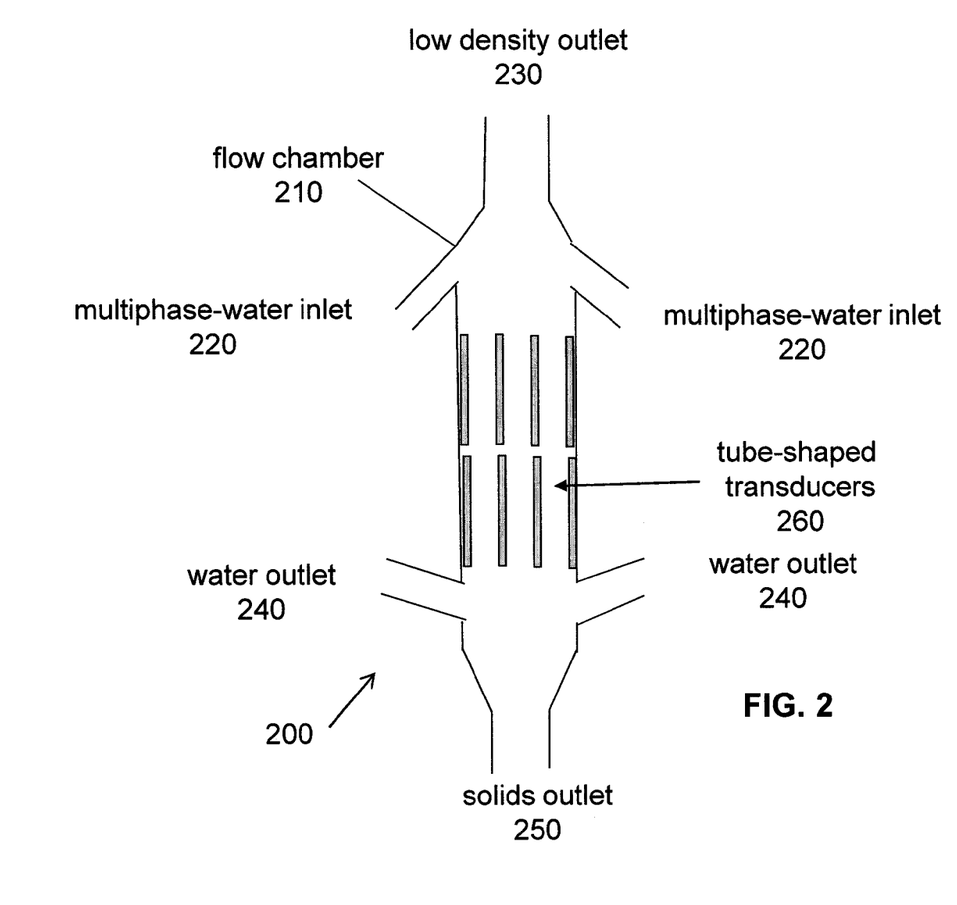
FIG. 2 is a schematic diagram of a first implementation having a parallel and/or serial array of tube-shaped transducers for agglomeration of and coalescence of suspended particles utilizing acoustic standing waves.
Figure 3:
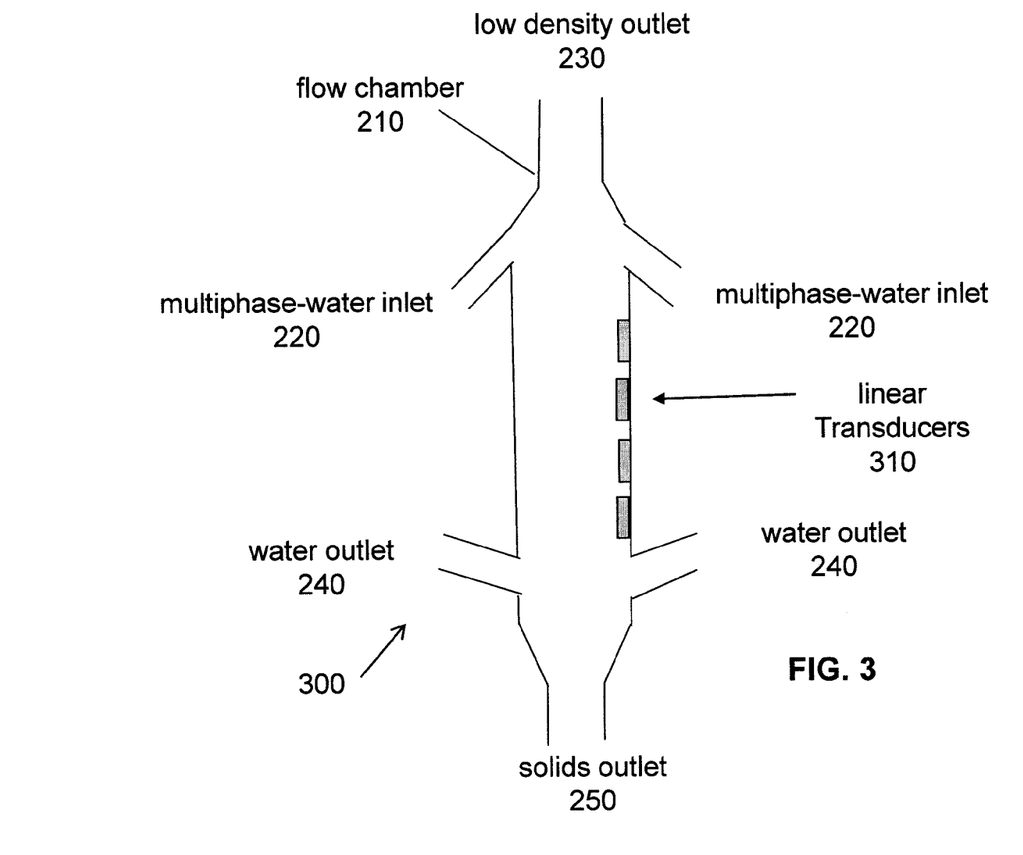
FIG. 3 is a schematic diagram of a second implementation in which there are flat transducers for agglomeration of and coalescence of suspended particles utilizing acoustic standing waves.
Figure 4A:
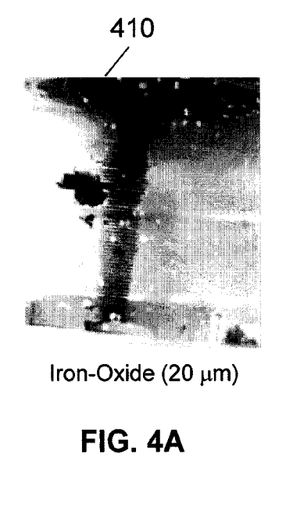
FIG. 4A is a photograph of collected iron oxide using a system such as that illustrated in FIGS. 2-3.
Figure 4B:
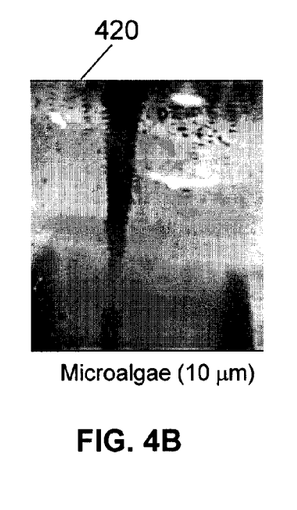
FIG. 4B is a photograph of collected microalgae using a system such as that illustrated in FIGS. 2-3.
Figure 4C:
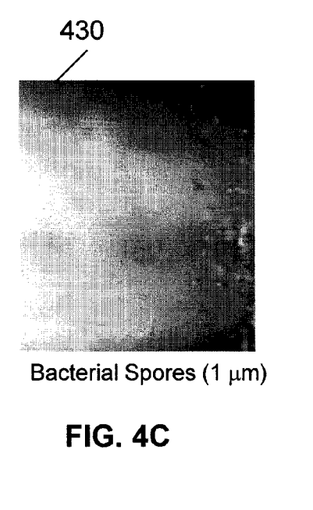
FIG. 4C is a photograph of collected bacterial spores using a system such as that illustrated in FIGS. 2-3.
Figure 4D:
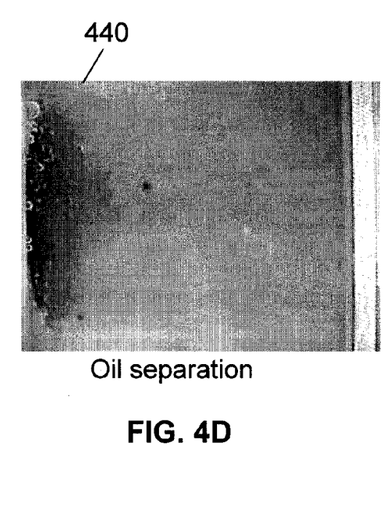
FIG. 4D is a photograph of separated oil using a system such as that illustrated in FIGS. 2-3.

The current subject matter allows for the simultaneous agglomeration of suspended solids such as microorganisms and dirt (metal oxides) and oil droplets. The ability to translate and concentrate these secondary phases is known as acoustophoresis. Described herein is an improved flow chamber with two different ultrasonic transducer arrangements. Diagrams 200, 300 respectively of FIGS. 2-3, show two different transducer arrangements for two variations of an overall-view of the current systems which utilize a series of solid cylindrical and hollow cylindrical transducers with the flowing water for particle agglomeration. A small experimental system put together by the inventors that demonstrate the concept is described below.

With reference to FIGS. 2 and 3, a flow chamber 210 is illustrated having a multi-phase water inlet 220, a low density outlet 230, a water outlet 240, and a solids outlet 250. It will be appreciated that there may be two or more of each inlet and outlet depending on the desired configuration and volumes being processed. Multi-phase water (i.e., water having suspended particulate, etc.) enters from the multi-phase water inlet 220 and exits as filtered water from water outlet 240. Particles and fluids having a low density, i.e., lower than the host fluid, such, as oils and other low-density fluids, exit from the low density outlet 230 and solids and other higher density particles exit from the solids outlet 250. An acoustic standing wave is generated in the middle of the flow chamber 210, either by a set of tube-shaped transducers 260 arranged in a parallel spacing within a center portion of the flow chamber or by an array of flat transducers 310, causes the particles (oil droplets) to agglomerate at the nodes (antinodes) in the acoustic wave. The agglomeration for high density particles will eventually result in their growing so as to overcome the acoustic pinning force and gravity settling causes them to fall into solids outlet 250. In the case of oil droplets the agglomeration at the antinodes will result in droplet coalescence and they will be able to overcome the acoustic pinning force and buoyancy force causes the larger droplets to drift to the low density outlet 230.

Several examples are shown in the photographs in FIGS. 4A-D. The first photo 410 shows the acoustophoretic collection of iron oxide particles, the second photograph 420 shows the collection of algae, the third photograph 430 shows the collection of bacterial spores, and the fourth photograph 440 shows the collection of oil droplets, all in a flowing water stream. A flat, circular transducer can, for example, be used in an acoustocollector to generate the collected matter in FIGS. 4A-D. The radial component of the pressure field of such a transducer is described by a Bessel function t whereas the axial component is described by a cosine function such as in the case of a one dimensional standing wave. The radial component acts to hold the captured algae in the column against the fluid flow drag force. The trapped algae are then further concentrated by inter-particles forces. The particles are then further separated from the flow by gravitational settling or by being driven to a collector pocket through a slow frequency sweeping method similar to that given in (i) B. Lipkens, M. Costolo, and E. Rietman, "The effect of frequency sweeping and fluid flow on particle trajectories in ultrasonic standing waves", IEEE Sensors Journal, Vol. 8, No. 6, pp. 667-677, 2008; (ii) Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008; and (iii) B. Lipkens, J. Dionne, A. Trask, B. Szczur, and E. Rietman, "Prediction and measurement of particle velocities in ultrasonic standing waves," J. Acoust. Soc. Am. 124, No. 4, pp. 2492 (A). The contents of each of the aforementioned papers are hereby fully incorporated by reference.

Physics of Acoustophoresis.

Acoustophoresis is the separation of a second phase (or phases) from a host fluid using sound pressure to create the driving force. An ultrasonic transducer operating at a fixed frequency f (Hz) is used to set up an acoustic standing wave in a fluid-filled cavity. A one dimensional standing wave is characterized by a local pressure p that is a function of position (x) and time (t), $$p(x,t) = P \cos(kx)\sin(\omega t), \quad (1)$$

where P is the amplitude of the acoustic pressure; k is the wavenumber ($=2\pi/\lambda$, where $\lambda$ is the wavelength), and $\omega = 2\pi f$, where $\omega$ is the angular frequency. The pressure of the acoustic wave produces an acoustic radiation force $F_{ac}$ on secondary-phase elements according to $$F_{ac} = X \pi R_p^3 k \frac{P^2}{\rho_f c_f^2} \sin(2kx), \quad (2)$$

where $R_p$ is the particle radius, $\rho_f$ is the density of the fluid medium, $c_f$ is the speed of sound in the fluid, and X is the acoustic contrast factor, defined by $$X = \frac{1}{3}\left[\frac{5\Lambda - 2}{1 + 2\Lambda} - \frac{1}{\sigma^2 \Lambda}\right], \quad (3)$$

where $\Lambda$ is the ratio of the particle density to fluid density and $\sigma$ is the ratio of the speed of sound in the particle to the sound speed in the fluid. The acoustic radiation force acts in the direction of the acoustic field. The acoustic radiation force is proportional to the product of acoustic pressure and acoustic pressure gradient. An inspection of the acoustic radiation force shows that it is proportional to the particle volume, frequency (or wavenumber), the acoustic energy density (or the square of the acoustic pressure amplitude), and the acoustic contrast factor. Note also that the spatial dependency has twice the periodicity of the acoustic field. The acoustic radiation force is thus a function of two mechanical properties, namely density and compressibility.

TABLE 1

Properties of water and 4 selected secondary phases.

| Material | $\rho$ (density) (kg/m³) | c (speed of sound in the medium) (m/s) | $\Lambda$ (dimensionless) | X (dimensionless) |
|---|---|---|---|---|
| Water | 1000 | 1509 | — | — |
| Hexanes | 720 | 1303 | 0.72 | −0.402 |
| Blood Cells | 1125 | 1900 | 1.125 | 0.185 |
| Bacterial Spores | 1100 | 1900 | 1.1 | 0.173 |
| Magnetic beads | 2000 | 1971 | 2.0 | 0.436 |

For three dimensional acoustic fields, a more general approach for calculating the acoustic radiation force is needed. Gor'kov's (1962) formulation can be used for this (see L. P. Gor'kov, "On the forces acting on a small particle in an acoustical field in an ideal fluid," Sov. Phys. Dokl., vol. 6, pp. 773-775, 1962). Gor'kov developed an expression for the acoustic radiation force $F_{ac}$ applicable to any sound field. The primary acoustic radiation force is defined as the gradient of a field potential U, given by $$F_{ac} = -\nabla(U), \quad (4)$$

where the field potential U is defined as $$U = V_0\left[\frac{\langle p^2(x, y, t)\rangle}{2\rho_f c_f^2}f_1 - \frac{3\rho_f \langle v^2(x, y, t)\rangle}{4}f_2\right], \quad (5)$$

and $f_1$ and $f_2$ are the monopole and dipole contributions defined by $$f_1 = 1 - \frac{1}{\Lambda \sigma^2}, \quad (6)$$

$$f_2 = \frac{2(\Lambda - 1)}{2\Lambda + 1},$$

where p(x,y,z,t) is the acoustic pressure, v(x,y,z,t) is the fluid particle velocity, and < > denote time averages. $V_o$ is the volume of the particle.

The diagram 100 of FIG. 1 shows the force required to separate small particles of various material properties. Each material has its own X parameter given in Equation [3]. In diagram 100, material properties (e.g. speed of sound, density) are used for the indicated material. The graph for bacteria spore is also valid for other materials of similar bulk modulus. Meaning smaller bacteria spore, very large protein clusters, and polystyrene microspheres would all be in this category. The blood cell curve is for any cells of similar bulk modulus. Finally the hexane curve would be valid for any tiny drops of oil-like material with the radius indicated on the curve. These curves are for, as an example, 1 MHz applied acoustic frequency and an acoustic pressure of 0.5 MPa. These are easily achieved control variables. Higher frequency and higher pressure will afford better separation of smaller particles—down to 10s of nm.

Simulations regarding the current subject matter were run by plotting the following equation:

$$\frac{n}{n_o} = \frac{\sin\left[2\arctan\left[\exp\left[-4\left(\frac{2\pi f}{c}\right)^2 E_{ac} R^2 Xt/(3\mu)\right]\tan\left(\frac{2\pi f}{c}x\right)\right]\right]}{\sin\left(\frac{4\pi f}{c}x\right)}$$

Where n is the number density of the suspended particulate, f is the frequency, c is the speed of sound, $E_{ac}$ is the energy density of the acoustic wave, R is the particle radius, X is the contrast factor, t is time, m is the dynamic viscosity of the fluid, and x is position in the standing wave. The equation describes the kinetics of the particles in the standing wave as a result of the action of the drag force and acoustic radiation force. This equation is derived in the paper by Feke et al.

The diagrams of FIGS. 5-10 plot the relative concentration, capture efficiency for different size particles of different densities and different frequencies. Along the x-axis is direction the particles travel from 0 to $\lambda/2$. The y-axis is the concentration relative to the initial of 1.

Figure 5:
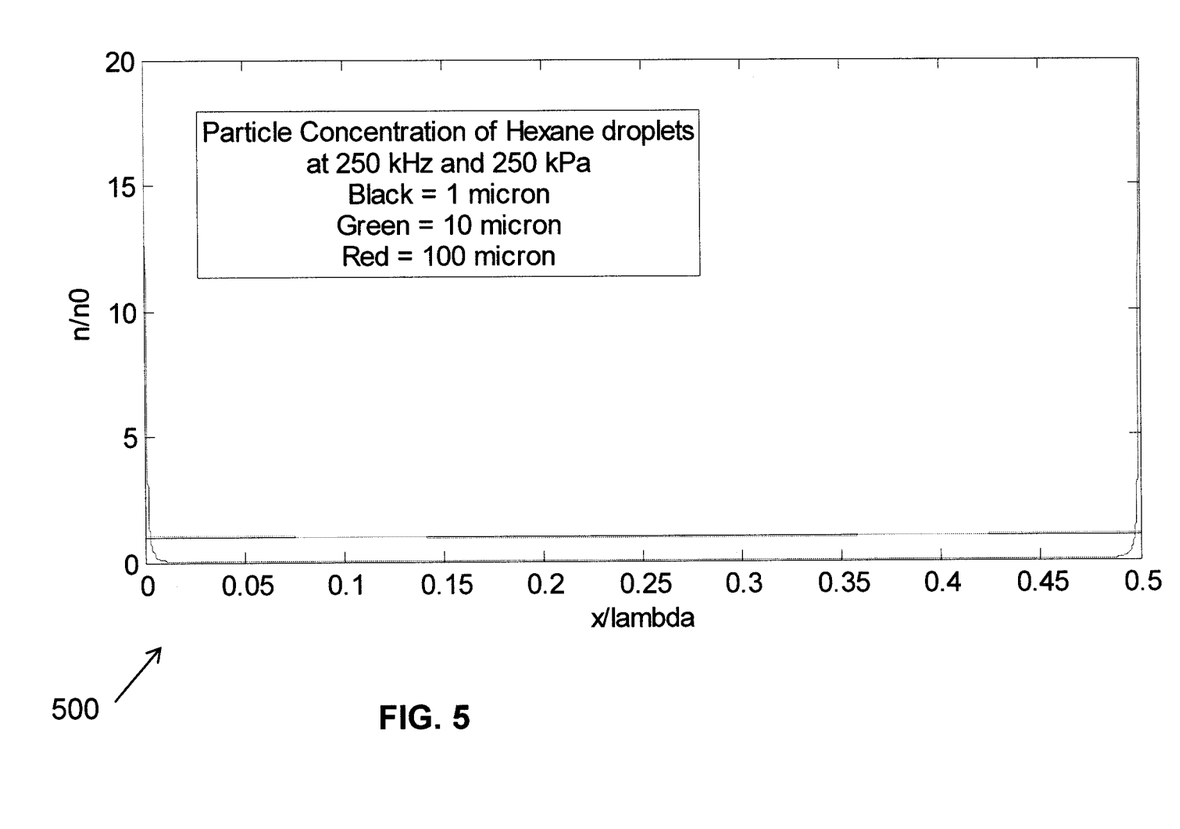
FIG. 5 is a diagram illustrating oil concentration at a transducer frequency of 250 kHz and exposure time of 0.1 s.
Figure 6:
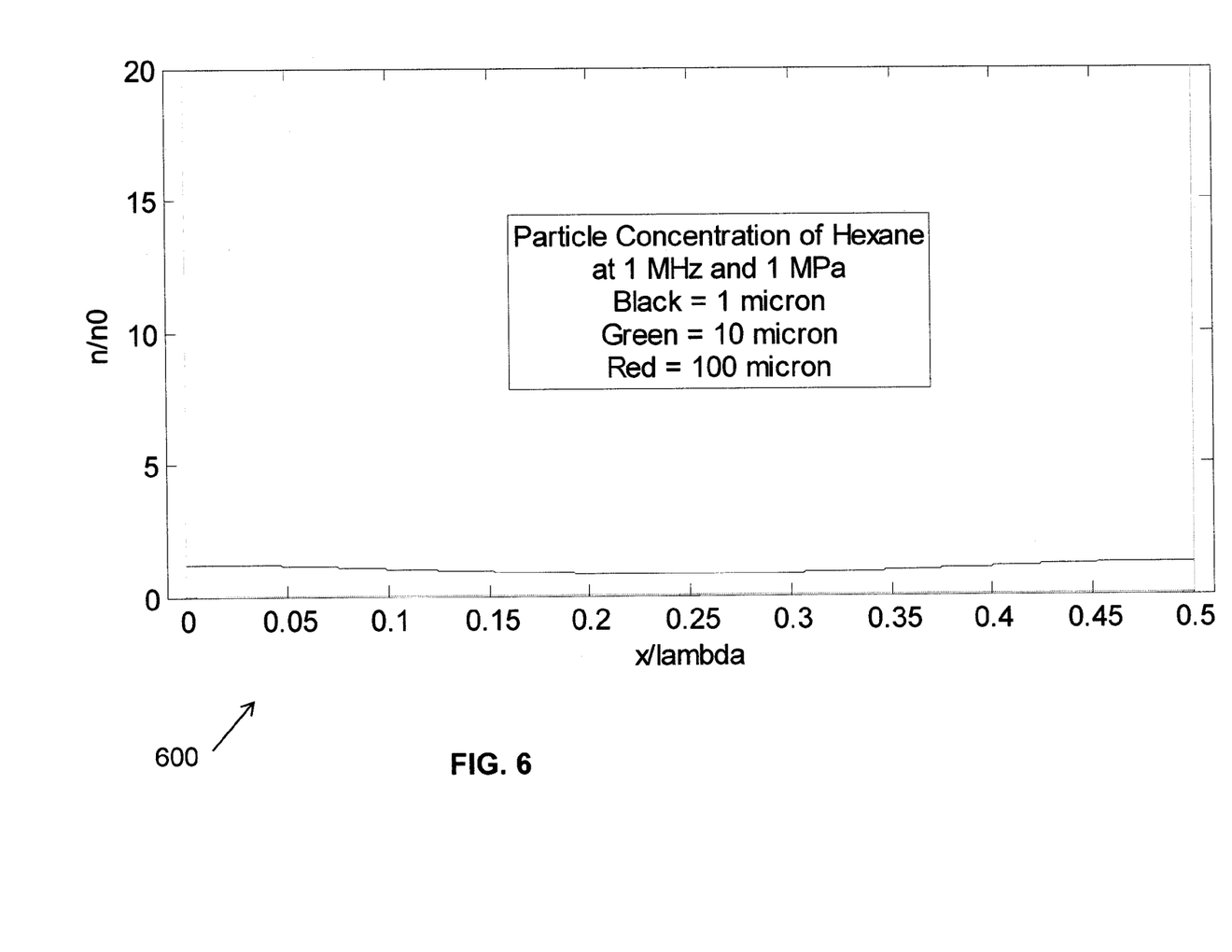
FIG. 6 is a diagram illustrating oil concentration at a transducer frequency of 1 MHz and exposure time of 0.1 s.
Figure 7:
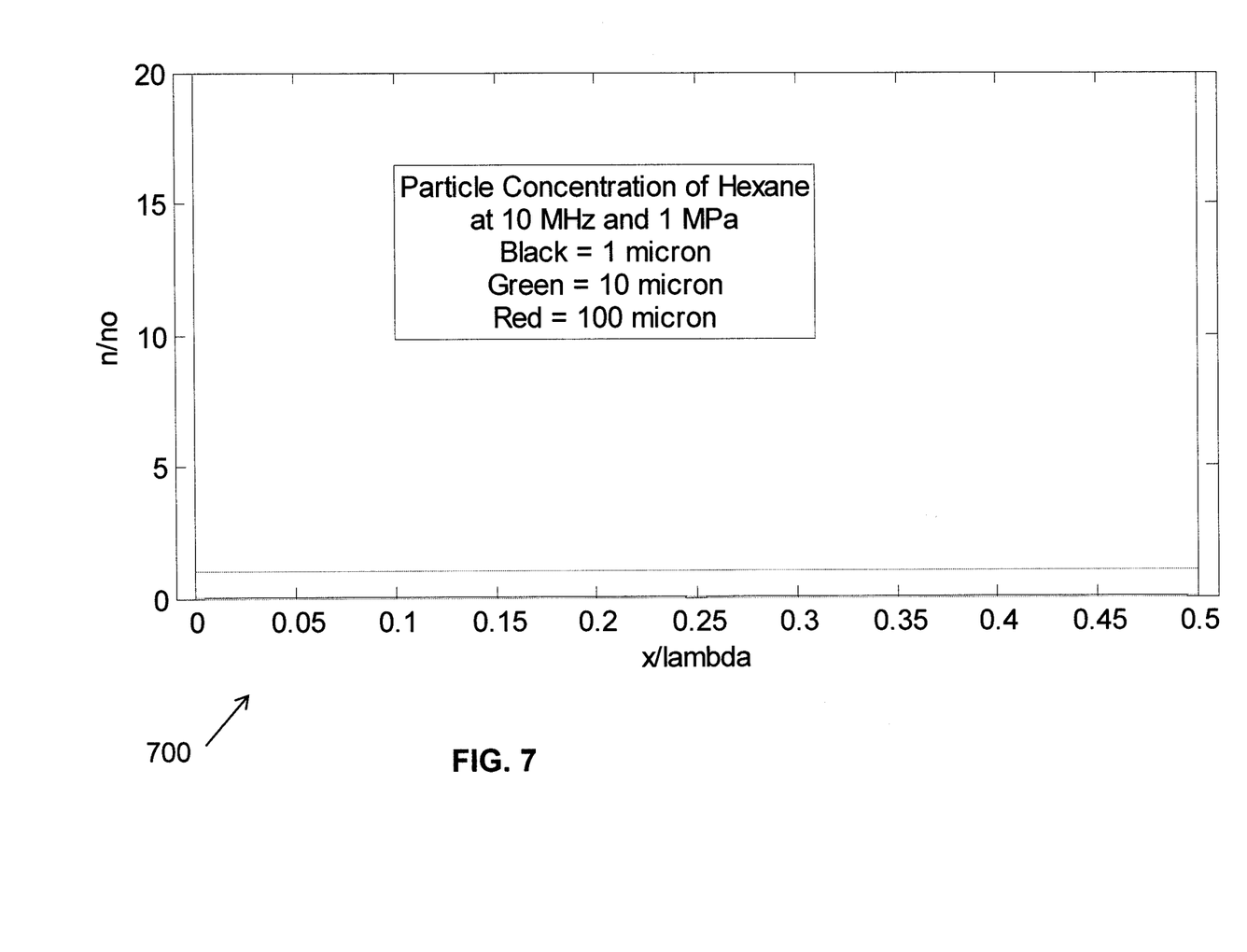
FIG. 7 is a diagram illustrating oil concentration at a transducer frequency of 10 MHz and exposure time of 0.1 s.

Diagram 500 of FIG. 5 shows the separation at 250 kHz for oil and an acoustic pressure amplitude of 250 kHz. Three particles sizes are shown; in black a 1 mm radius particle, in green a 10 mm radius particle, and in red a 100 mm radius particle. We see that the large droplets are heavily concentrated at the pressure anti-nodal planes of the standing wave, whereas the intermediate and small particle have not undergone any appreciable concentration. This situation can be used to selectively concentrate and separate large particles, and exhibits size-exclusion behavior. Diagram 600 of FIG. 6 shows separation at 1 MHz for oil. Here one can see a concentration efficiency of much greater than 20:1 for the intermediate and large droplets, and only minor changes for the small droplets. Finally, diagram 700 of FIG. 7 shows separation at 10 MHz, where the intermediate and small particles are heavily concentrated, but not the large ones. This is caused by the fact that the large particles are of the same order as the wavelength, and the acoustic radiation force is no longer effective. This is significant, because it shows a size-exclusion behavior that can be further exploited for preparation of very fine emulsions of biologically significant agents.

Figure 8:
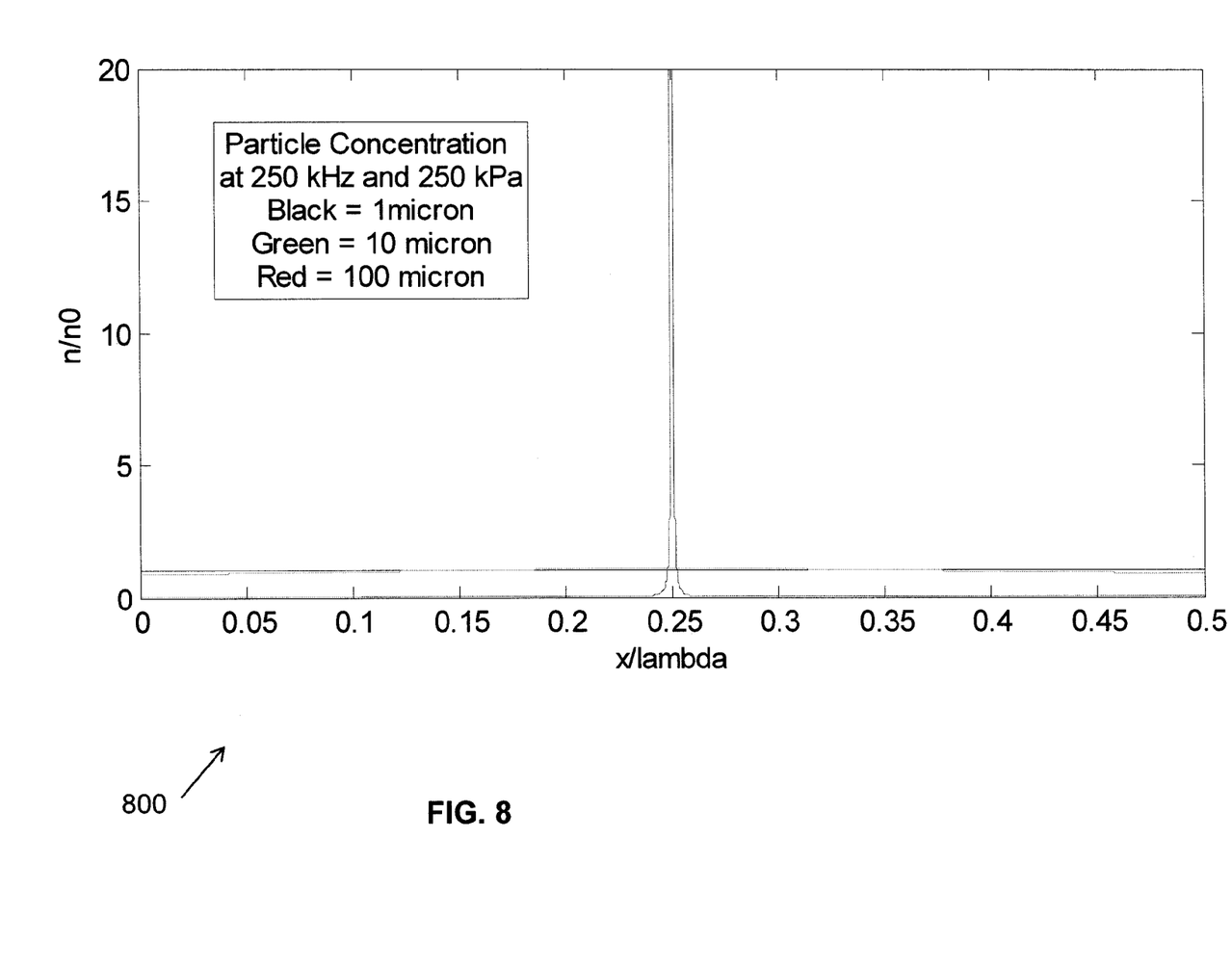
FIG. 8 is a diagram illustrating magnetic beads concentration at a transducer frequency of 250 kHz and exposure time of 0.1 s.
Figure 9:
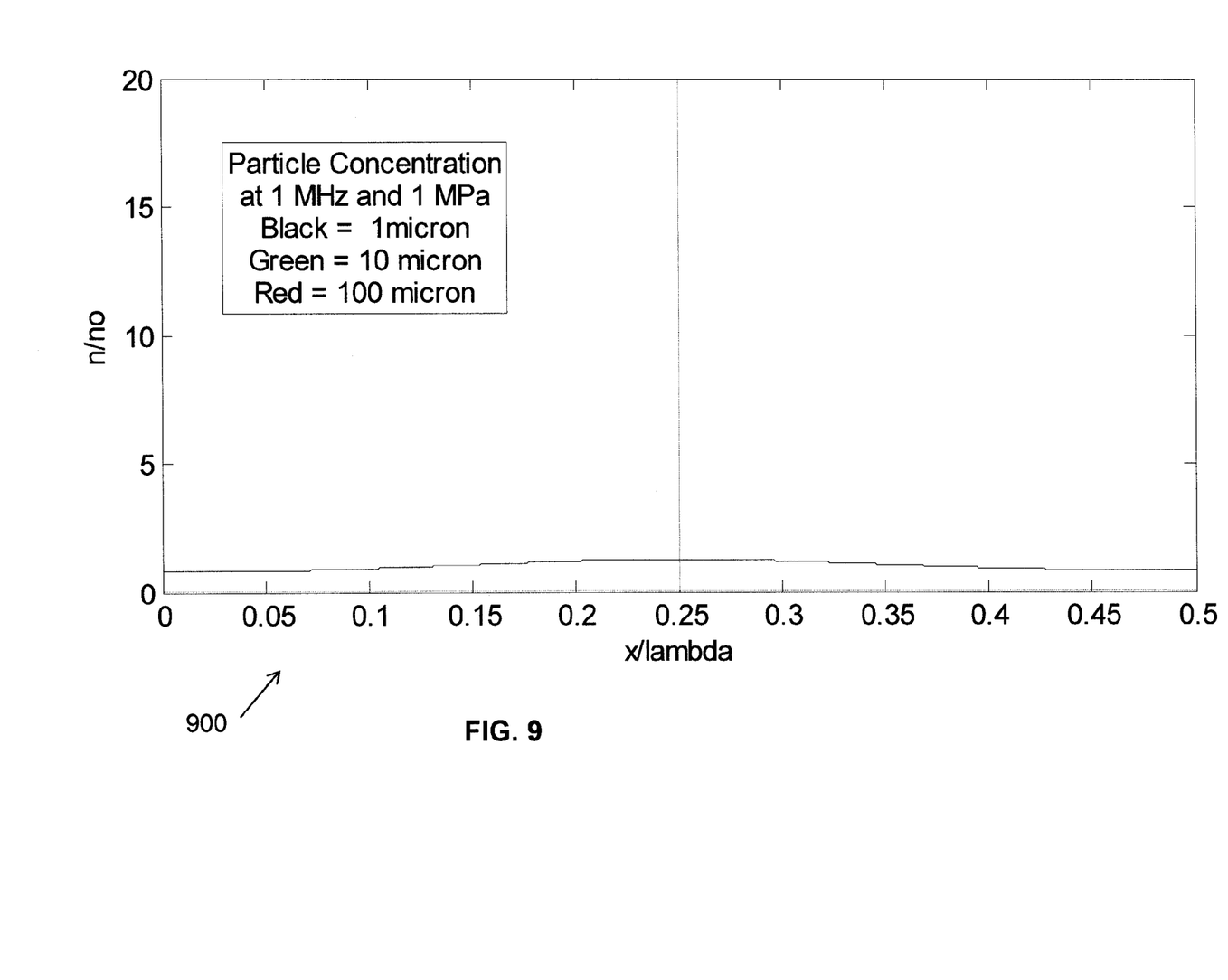
FIG. 9 is a diagram illustrating magnetic beads separation at a transducer frequency of 1 MHz and exposure time of 0.1 s.
Figure 10:
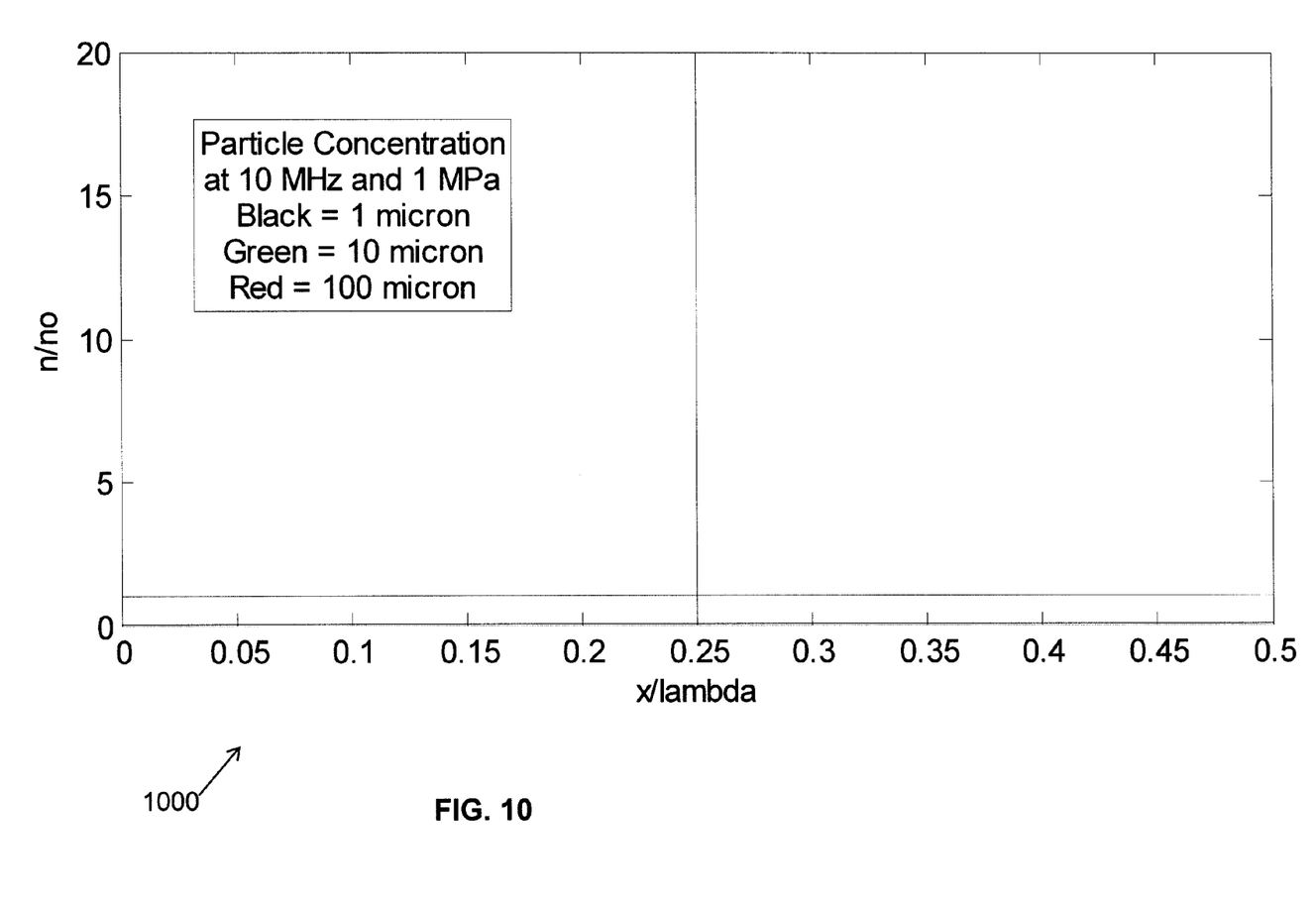
FIG. 10 is a diagram illustrating magnetic beads separation at a transducer frequency of 10 MHz and exposure time of 0.1 s.

FIGS. 8-10 show analogous conditions for iron oxide ($FeO_2$, a metal oxide simulant). Diagram 800 of FIG. 8 shows concentration at 250 kHz and 250 kPa for large, intermediate, and small particles of 100, 10, and 1 micron. We observe that particles with positive contrast move to the pressure nodes. It also shows that the large particles are concentrated significantly at the pressure nodes, and intermediate and smaller particles are not concentrated. Therefore, size-exclusion can work here as well. Diagram 900 of FIG. 9 shows the concentration at 1 MHz and 1 MPa, and shows that large and intermediate particles are concentrated but not small ones. Finally, diagram 1000 of FIG. 10 shows concentration at 10 MHz, where intermediate and small particles are concentrated. The large particles are of similar magnitude as the wavelength and do not experience significant concentration. Analogous behavior is observed for micro-algae, bacteria, and blood cells. Like the oil case above, this is also significant because it demonstrates that the current subject matter can be applied for biotechnology applications for separating species of various sizes, essentially a high-flow, large-volume, size-exclusion separation technology. It also shows promise for lipid and platelet separation of blood.

As described above, two approaches to concentrating the particles through acoustic standing wave agglomeration (or coalescence). (1) The first approach as illustrated in FIG. 2 involves a series involves a parallel array of tube-shaped transducers. (2) The second approach as illustrated in FIG. 3 uses a series of flat acoustic transducers operating at 1 MHz and 10 MHz. Notwithstanding, it will be appreciated that other arrangements of acoustic transducers can be utilized.

Figure 11:
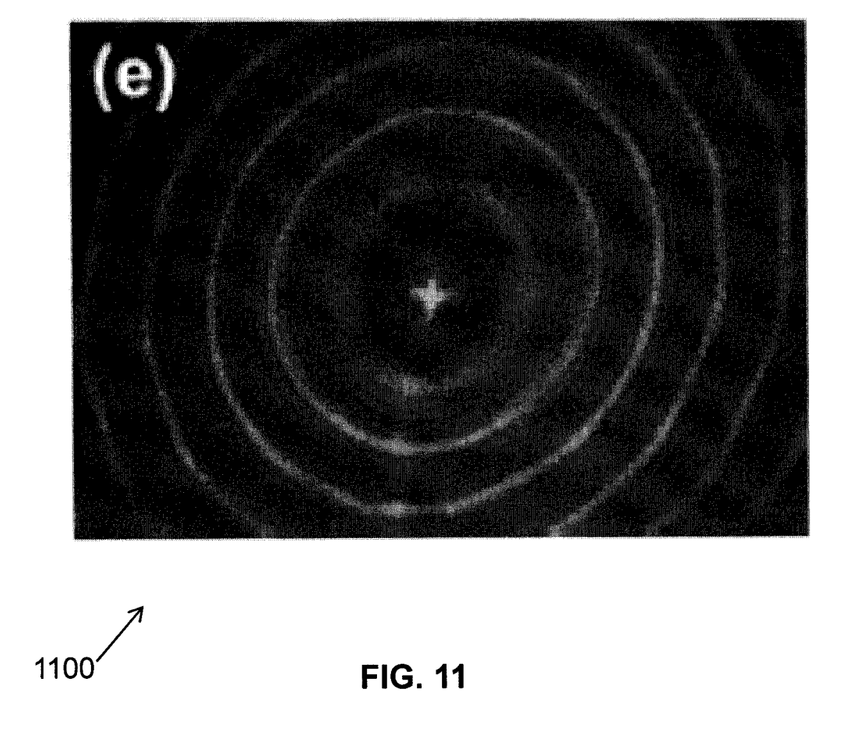
FIG. 11: is a photograph illustrating an acoustic standing wave in a tube shaped transducer.

The first implementation is shown in FIG. 2 with further details in the diagram 1100 of FIG. 11. With this arrangement, a multiphase-water mixture is pumped into the flow chamber 210 via the multi-phase water inlet 220 device from the where it encounters a parallel array of tube-shaped transducers 260 each operating at 1-10 MHz frequency. When the solution encounters the array of tube transducers 260 the agglomeration occurs and due to gravity the large clumps fall into the solids outlet 250 (e.g., a collection port, etc.). Any coalesced oil, or oil-like substances, will overcome buoyancy and self-transport to the respective low density outlet 230 on the top of the flow chamber 210. Diagram 1100 of FIG. 11 shows pressure nodes in the tube-shaped transducer array 260.

With the second approach, as shown in FIG. 3, a multiphase-water mixture is pumped into the flow chamber 210 via the multi-phase water inlet 220 where it encounters a serial array of flat 1 cm transducers 310 operating at a frequency range between 1 and 10 MHz. Like the first approach, when the solution encounters the array of tube transducers 310 the agglomeration occurs and due to gravity the large clumps fall into the solids outlet 250 (e.g., a collection port, etc.). Any coalesced oil, or oil-like substances, will overcome buoyancy and self-transport to the low density outlet 230 on the top of the flow chamber 210. As used herein, unless otherwise stated, the term outlet can comprise a piped exit from the flow chamber 210 or it can comprise a collection port requiring periodic removal of separated particulate.

While this specification contains many specifics, these should not be construed as limitations on the scope of what is claimed or of what may be claimed, but rather as descriptions of features specific to particular variations. Certain features that are described in this specification in the context of separate variations can also be implemented in combination in a single variation. Conversely, various features that are described in the context of a single variation can also be implemented in multiple variations separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:
1. An apparatus comprising:
   a flow chamber through which a mixture of a fluid and either particulates or droplets flow at high volume flow rates, the flow chamber comprising:

at least one multi-phase fluid inlet through which multi-phase fluid enters the flow chamber;

a fluid outlet through which fluid exits the flow chamber;

a solids outlet through which particulates or droplets having a density at or above a pre-defined threshold exit the flow chamber; and a low density outlet through which particulates or droplets having a density below the pre-defined threshold exit the flow chamber;

one or more ultrasonic transducers; and one or more reflectors corresponding to each transducer;

wherein each transducer is configured to form a three-dimensional acoustic field at a different ultrasonic frequency and each ultrasonic frequency is optimized for a specific range of particulate sizes to, along with a geometry of the flow chamber, selectively separate particulates or droplets from the multi-phase fluid by continuously causing particulates or droplets to agglomerate, coalesce, cluster, clump, or grow and increase in size such that they continuously fall out of the acoustic field due to gravity and exit the flow chamber via the solids outlet or rise out of the acoustic field due to buoyancy forces and exit the flow chamber via the low density outlet.

2. An apparatus as in claim 1, wherein the one or more ultrasonic transducers operate at a frequency in a range of 1 MHz to 10 MHz.

3. An apparatus as in claim 1, wherein the one or more ultrasonic transducers operate at a frequency in a range of 100 kHz to 20 MHz.

4. An apparatus as in claim 1, wherein the one or more ultrasonic transducers are embedded in a wall of the flow chamber.

5. An apparatus as in claim 3, wherein the one or more ultrasonic transducers are arranged in a flat series.

6. An apparatus as in claim 1, wherein there are two or more ultrasonic transducers that are arranged in a parallel array within an inner portion of the flow chamber.

7. An apparatus as in claim 1, wherein the flow chamber is vertically oriented with the low density outlet being on an upper portion and the solids outlet being on a lower portion.

8. An apparatus as in claim 1 wherein the flow chamber is horizontally oriented with the low density outlet being on the upper portion and the solids outlet being on the lower portion.

9. An apparatus as in claim 1 wherein the flow chamber is diagonally oriented with the low density outlet being on the upper incline and the solids outlet being on the lower incline.

10. An apparatus as in claim 6, wherein the multi-phase fluid inlet is disposed between the low density outlet and the two or more ultrasonic transducers.

11. An apparatus as in claim 6, wherein the multi-phase fluid inlet is at an acute angle from an outer wall of the flow chamber relative to the solids outlet.

12. An apparatus as in claim 7, wherein the fluid outlet is disposed between the two or more ultrasonic transducers and the solids outlet.

13. An apparatus as in claim 9, wherein the multi-phase fluid inlet is at an obtuse angle from an outer wall of the flow chamber relative to the solids outlet.

14. An apparatus as in claim 1, wherein the particles are selected from the group consisting of microalgae, yeast, fungi, bacteria, spores, gases or oils, metal oxides, metal particles, clays, dirt, plastics, and any particulate with a non-zero contrast factor.

15. An apparatus as in claim 1, wherein each transducer is optimized for a specific range of particles selected from the group consisting of microalgae, yeast, fungi, bacteria, spores, gases or oils, metal oxides, metal particles, clays, dirt, plastics, and any particulate with a non-zero contrast factor.

16. An apparatus as in claim 1, wherein the one or more ultrasonic transducers each generate a three-dimensional acoustic field perpendicular to the direction of the mean flow in the flow channel.

17. An apparatus as in claim 13, wherein the one or more three-dimensional acoustic fields have a horizontal orientation.

18. An apparatus as in claim 13, wherein the one or more three-dimensional acoustic fields have a vertical orientation.

19. An apparatus as in claim 13, wherein the one or more three-dimensional acoustic fields exert acoustic radiation force on the particulate for which the ultrasonic frequency is optimized for, such that the particulate is trapped in its corresponding three-dimensional acoustic field against a fluid drag force, and wherein the particulate is concentrated in the acoustic field over time.

20. An apparatus as in claim 1, wherein the solids outlet is tapered.

21. An apparatus as in claim 1, wherein the flow chamber is oriented such that the multi-phase fluid is gravity fed from the multi-phase fluid inlet towards the solids outlet.

22. A method of separating particulate and/or droplets from a fluid comprising:

flowing the fluid past one or more positions within a flow chamber at a flow rate of up to 120 mL/min; and forming three-dimensional acoustic fields at the one or more positions, wherein each three-dimensional acoustic field is maintained at a different ultrasonic frequency, wherein each ultrasonic frequency is optimized for a specific range of particulate or droplet sizes and wherein particulates and/or droplets of an optimized size are trapped in their corresponding three-dimensional acoustic field against the flow of the fluid, thereby clustering the particulates in their corresponding three-dimensional acoustic field such that the clustered particulates and/or droplets increase in size and they continuously fall out of the acoustic field due to gravity or rise out due to buoyancy forces and cause the clustered particulates and/or droplets to exit the flow chamber;

wherein the flow chamber comprises:

at least one multi-phase fluid inlet through which multi-phase fluid enters the flow chamber;

a fluid outlet through which fluid exits the flow chamber, the at least one multi-phase fluid inlet being located above the fluid outlet;

a solids outlet through which particulates or droplets having a density at or above a pre-defined threshold exit the flow chamber; and a low density outlet through which particulates or droplets having a density below the pre-defined threshold exit the flow chamber, the low density outlet being located above the solids outlet and the at least one multi-phase fluid inlet;

one or more ultrasonic transducers located between the fluid outlet and the multi-phase fluid inlet; and one or more reflectors corresponding to each transducer.

23. An apparatus comprising:

a flow chamber through which is flowed a mixture of a fluid and a particulate at a rate of up to 120 mL/minute, the flow chamber comprising:

at least one multi-phase fluid inlet through which multi-phase fluid enters the flow chamber;

a fluid outlet through which fluid exits the flow chamber;

a solids outlet through which clustered particulates or droplets having a density at or above a pre-defined threshold exit the flow chamber, the solids outlet being located on a lower portion of the flow chamber; and a low density outlet through which clustered particulates or droplets having a density below the pre-defined threshold exit the flow chamber, the low density outlet being located above the at least one multi-phase fluid inlet on an upper portion of the flow chamber;

one or more ultrasonic transducers located between the fluid outlet and the multi-phase water outlet; and one or more reflectors corresponding to each transducer;

wherein the multi-phase fluid inlet is located between the low density outlet and the one or more ultrasonic transducers;

wherein the fluid outlet is located between the one or more ultrasonic transducers and the solids outlet;

wherein the multi-phase fluid inlet is at an acute angle from an outer wall of the flow chamber relative to the solids outlet;

wherein each transducer is configured to form a three-dimensional acoustic field at a different ultrasonic frequency and each ultrasonic frequency is optimized for a specific range of particle sizes to, along with a geometry of the flow chamber, cause particulates or droplets to cluster and increase in size such that they continuously fall out of the acoustic field due to gravity or rise out due to buoyancy forces and cause the clustered particulates or droplets to exit the flow chamber via one of the solids outlet and the low density outlet.

24. The apparatus of claim 1, wherein the apparatus operates at flow rates of up to about 14,000 mL/min.

25. The method of claim 22, wherein the ultrasonic frequency for each three-dimensional acoustic field is selected to maximize the acoustic radiation force applied to particulates and/or droplets of a given density according to Gorkov's formulation:

$$F_{ac} = -\nabla(U)$$
$$U = V_0\left[\frac{\langle p^2(x, y, z, t)\rangle}{2\rho_f c_f^2}f_1 - \frac{3\rho_f\langle u^2(x, y, z, t)\rangle}{4}f_2\right]$$
$$f_1 = 1 - \frac{1}{\Lambda\sigma^2} \quad f_2 = \frac{2(\Lambda - 1)}{2\Lambda + 1}$$

wherein $F_{ac}$ is the acoustic radiation force; U is the field potential; $V_0$ is the volume of the particle; p(x,y,z,t) is the acoustic pressure; v(x,y,z,t) is the fluid particle velocity; < > denote time averages; $\rho_f$ is the density of the fluid; $c_f$ is the speed of sound in the fluid; $\Lambda$ is the ratio of the particulates and/or droplets density to fluid density; and $\sigma$ is the ratio of the speed of sound in the particulates and/or droplets to the speed of sound in the fluid.

26. An apparatus comprising:
a flow chamber through which is flowed a mixture of a fluid and a particulate at a rate of up to 120 mL/minute, the flow chamber comprising:

at least one multi-phase fluid inlet through which multi-phase fluid enters the flow chamber;

a fluid outlet through which fluid exits the flow chamber;

a solids outlet through which agglomerated particulates and/or droplets having a density at or above a pre-defined threshold exit the flow chamber, the solids outlet being located on a lower portion of the flow chamber; and a low density outlet through which agglomerated particulates and/or droplets having a density below the pre-defined threshold exit the flow chamber, the low density outlet being located above the at least one multi-phase fluid inlet on an upper portion of the flow chamber;

one or more ultrasonic transducers located between the fluid outlet and the multi-phase water outlet; and one or more reflectors corresponding to each transducer;

wherein the multi-phase fluid inlet is located between the low density outlet and the one or more ultrasonic transducers;

wherein the fluid outlet is located between the one or more ultrasonic transducers and the solids outlet;

wherein the multi-phase fluid inlet is at an acute angle from an outer wall of the flow chamber relative to the solids outlet;

wherein each transducer forms a three-dimensional acoustic field that causes particulates and/or droplets to agglomerate and increase in size such that gravity or buoyancy forces cause the agglomerated particulates and/or droplets to exit the flow chamber via one of the solids outlet and the low density outlet; and wherein the apparatus is configured to select the ultrasonic frequency for each three-dimensional acoustic field to maximize the acoustic radiation force applied to particulates and/or droplets of a given density according to Gorkov's formulation:

$$F_{ac} = -\nabla(U)$$
$$U = V_0\left[\frac{\langle p^2(x, y, z, t)\rangle}{2\rho_f c_f^2}f_1 - \frac{3\rho_f\langle u^2(x, y, z, t)\rangle}{4}f_2\right]$$
$$f_1 = 1 - \frac{1}{\Lambda\sigma^2} \quad f_2 = \frac{2(\Lambda - 1)}{2\Lambda + 1}$$

wherein $F_{ac}$ is the acoustic radiation force; U is the field potential; $V_0$ is the volume of the particle; p(x,y,z,t) is the acoustic pressure; v(x,y,z,t) is the fluid particulates or droplets velocity; < > denote time averages; $\rho_f$ is the density of the fluid; $c_f$ is the speed of sound in the fluid; $\Lambda$ is the ratio of the particulates or droplets density to fluid density; and $\sigma$ is the ratio of the speed of sound in the particulates or droplets to the speed of sound in the fluid.

* * * * *